United States Patent [19]

Mar

[11] 4,288,229
[45] Sep. 8, 1981

[54] DETERMINATION OF TOTAL ORGANIC CARBON IN A PLURALITY OF AQUEOUS SAMPLES CONTAINING HALIDE ION

[75] Inventor: Danny M. Mar, Daly City, Calif.

[73] Assignee: Envirotech Corporation, Menlo Park, Calif.

[21] Appl. No.: 142,577

[22] Filed: Apr. 21, 1980

Related U.S. Application Data

[63] Continuation-in-part of Ser. No. 128,066, Mar. 7, 1980.

[51] Int. Cl.$^3$ .................... G01N 33/18; G01N 31/12
[52] U.S. Cl. .......................... 23/230 PC; 23/906; 422/79; 422/81
[58] Field of Search ............ 23/230 PC, 906; 422/79, 422/81

[56] References Cited

U.S. PATENT DOCUMENTS

| | | | |
|---|---|---|---|
| 3,784,359 | 1/1974 | Parth | 422/79 |
| 3,854,881 | 12/1974 | Cohen | 422/79 |
| 3,955,924 | 5/1976 | Northmore et al. | 422/79 X |
| 4,217,108 | 8/1980 | Melzer et al. | 23/906 |

OTHER PUBLICATIONS

Ehrhardt, "A New Method for the Automatic Measurement of Dissolved Organic Carbon in Sea Water," *Deep-Sea Research*, vol. 16, pp. 393–397, (1969).

"Ein neues Verfahren zur Bestimmung von Organisch gebundenem Kohlenstoff im Wasser durch photochemische Oxidation", Vom Wasser, vol. 43, pp. 315–325, (1974).

*Primary Examiner*—Ronald Serwin
*Attorney, Agent, or Firm*—Robert E. Krebs; T. J. McNaughton

[57] ABSTRACT

Total organic carbon can be determined for each one of a plurality of discrete aqueous samples containing halide ion by means of an apparatus comprising a reactor (13), and a pump (12) and flowline (11) for introducing a continuous flow into the reactor (13) of a solution that contains an oxidizing agent and mercuric monohalide ion without forming an insoluble precipitate. The solution to be introduced into the reactor (13) is prepared by mixing the oxidizing agent with a solution containing mercuric monohalide ion; and the solution containing mercuric monohalide ion is formed by adding a quantity of mercuric halide and a quantity of mercuric nitrate to an aqueous solution containing nitric acid, where the molar concentration of the mercuric halide is at least equal to the molar concentration of the mercuric nitrate. The samples are introduced in succession into the reactor (13), either by means of a syringe injection port (19) in the flowline (11), or by means of a rotary valve (203) and sample loop (204) in a recirculation line (202) through which carbon-free liquid is withdrawn from and circulated back to the reactor (13). A mercury vapor lamp (17) is immersed in the liquid in the reactor (13) for irradiating the oxidizing agent and each sample in the reactor (13) with ultraviolet energy in order to oxidize any organic matter in the sample to carbon dioxide. A sparger (20) is provided to remove the carbon dioxide so produced from the reactor (13); and a carbon dioxide detector (24) detects the carbon dioxide so removed. Electronic integrator circuitry (25) provides a measure of total carbon in the carbon dioxide produced in the oxidation interval for each sample.

23 Claims, 3 Drawing Figures

DETERMINATION OF TOTAL ORGANIC CARBON IN A PLURALITY OF AQUEOUS SAMPLES CONTAINING HALIDE ION

This application is a continuation-in-part of copending patent application Ser. No. 128,066 filed on Mar. 7, 1980.

BACKGROUND OF THE INVENTION

1. Field of the Invention

This invention pertains to the determination of total organic carbon in each one of a plurality of discrete aqueous samples containing halide ion, e.g., a plurality of seawater samples.

2. State of the Prior Art

A technique for determining total organic carbon (TOC) in a seawater sample was described in an article by M. Erhardt entitled "A New Method for the Automatic Measurement of Dissolved Organic Carbon in Sea Water" published in *Deep-Sea Research*, Vol. 16, pages 393–397 (1969), in which dissolved organic matter in the sample is oxidized with a persulfate oxidizing agent using ultraviolet radiation to promote the oxidation, and in which carbon dioxide formed by oxidation of the organic matter is quantitatively detected to determine total carbon.

TOC in an aqueous sample containing dissolved organic matter has been determined by irradiating the sample with ultraviolet radiation from a low-pressure mercury vapor lamp immersed in the sample in order to oxidize the organic matter to carbon dioxide, sparging the carbon dioxide so produced from the reactor, and then measuring total carbon in the sparged carbon dioxide. Such a technique was described in an article by P. Wolfel and H. Sontheimer entitled "Ein neues Verfahren zur Bestimmung von organisch gebundenem Kohlenstoff im Wasser durch photochemische Oxidation" published in *Vom Wasser*, Vol. 43, pages 315–325 (1974).

In co-pending U.S. patent application Ser. No. 127,333, a technique was described for determining total carbon in each one of a plurality of liquid samples by maintaining a continuous flow of a liquid containing an oxidizing agent (e.g., persulfate ion $S_2O_8^{--}$ or hydroxy free radical .OH) through a reactor into which the samples are introduced in succession, and by irradiating each sample in the reactor with ultraviolet radiation from a mercury vapor lamp immersed in the sample to oxidize carbonaceous matter in the sample and thereby produce carbon dioxide that can be measured for total carbon.

In chemical oxygen demand (COD) analysis, where dichromate ion is used as the oxidizing agent, free chloride ion $Cl^-$ in a sample would react with the oxidizing agent, thereby decreasing the amount of oxidizing agent available for the analysis. It was known, however, that by adding mercuric sulfate $HgSO_4$ to the sample, free $Cl^-$ would be complexed with $Hg^{++}$ to form mercuric chloride $HgCl_2$, thereby removing free $Cl^-$ from interfering with the analysis. However, adding $HgSO_4$ to an aqueous sample containing persulfate ion $S_2O_8^{--}$ produces an insoluble precipitate, i.e., mercuric oxide $HgO$, which cannot react with chloride ion $Cl^-$.

It was known that mercuric monochloride ion $HgCl^+$ can be formed by mixing equal molar concentrations of mercuric chloride $HgCl_2$ and mercuric nitrate $Hg(NO_3)_2$ together in aqueous solution. However, $HgCl^+$ is not usually used to complex free chloride ion $Cl^-$ for analytical purposes. Use of a solution containing $HgCl^+$ for complexing free chloride ion $Cl^-$ appears to have had no practical application until the present invention.

OBJECTS OF THE INVENTION

It is an object of the present invention to provide a technique for determining total organic carbon in each one of a plurality of discrete aqueous samples containing halide ion, using a reagent that oxidizes organic matter in each sample in succession in the presence of ultraviolet radiation, where the rate of oxidation of the organic matter in each sample is not significantly suppressed due to halide ion interference.

It is a particular object of the present invention to provide a technique for determining total organic carbon in each one of a plurality of discrete aqueous samples containing halide ion by ultraviolet-promoted oxidation of organic matter in each sample, using persulfate ion as an oxidizing agent, where suppression of the rate of oxidation of the organic matter due to halide ion interference is minimal.

In accordance with the present invention, each sample is introduced in succession into a reactor in which a source of ultraviolet radiation is disposed, and a continuous flow of a precipitate-free aqueous solution containing an oxidizing agent and mercuric monohalide ion is supplied to the reactor. The ultraviolet radiation causes oxidation of the organic carbon in each sample to carbon dioxide, and the carbon dioxide so produced is removed from the reactor and is measured for total carbon. A uniformly adequate supply of oxidizing agent is continuously available in the reactor to insure complete oxidation of the organic carbon in each liquid sample.

In one embodiment of the present invention, the samples to be analyzed are introduced in succession into a flowline that carries the aqueous solution containing the oxidizing agent and mercuric monohalide ion into the reactor. In this embodiment, the flow rates of the solution and of a sample in the flowline are additive; and any background carbon present in the solution remains constant as each successive sample is conveyed into the reactor by the continuously flowing solution.

In an alternative embodiment of the present invention, a quantity of carbon-free liquid is drawn from the reactor and returned to the reactor through a recirculation line; and the samples to be analyzed are introduced in succession into the recirculating line for conveyance into the reactor by the carbon-free liquid circulating in the recirculation line.

In accordance with the present invention, carbon dioxide produced by oxidation of organic matter in each successive sample is sparged from the reactor. The sparged carbon dioxide is then analyzed by conventional means for total carbon, thereby providing a measure of total organic carbon in each sample.

DESCRIPTION OF THE DRAWING

FIG. 3 is a schematic representation of a portion of a system having an alternative means for determining total carbon in gas sparged from a reactor following oxidation of organic matter in the reactor.

DESCRIPTION OF THE PREFERRED EMBODIMENTS

Figure 1:
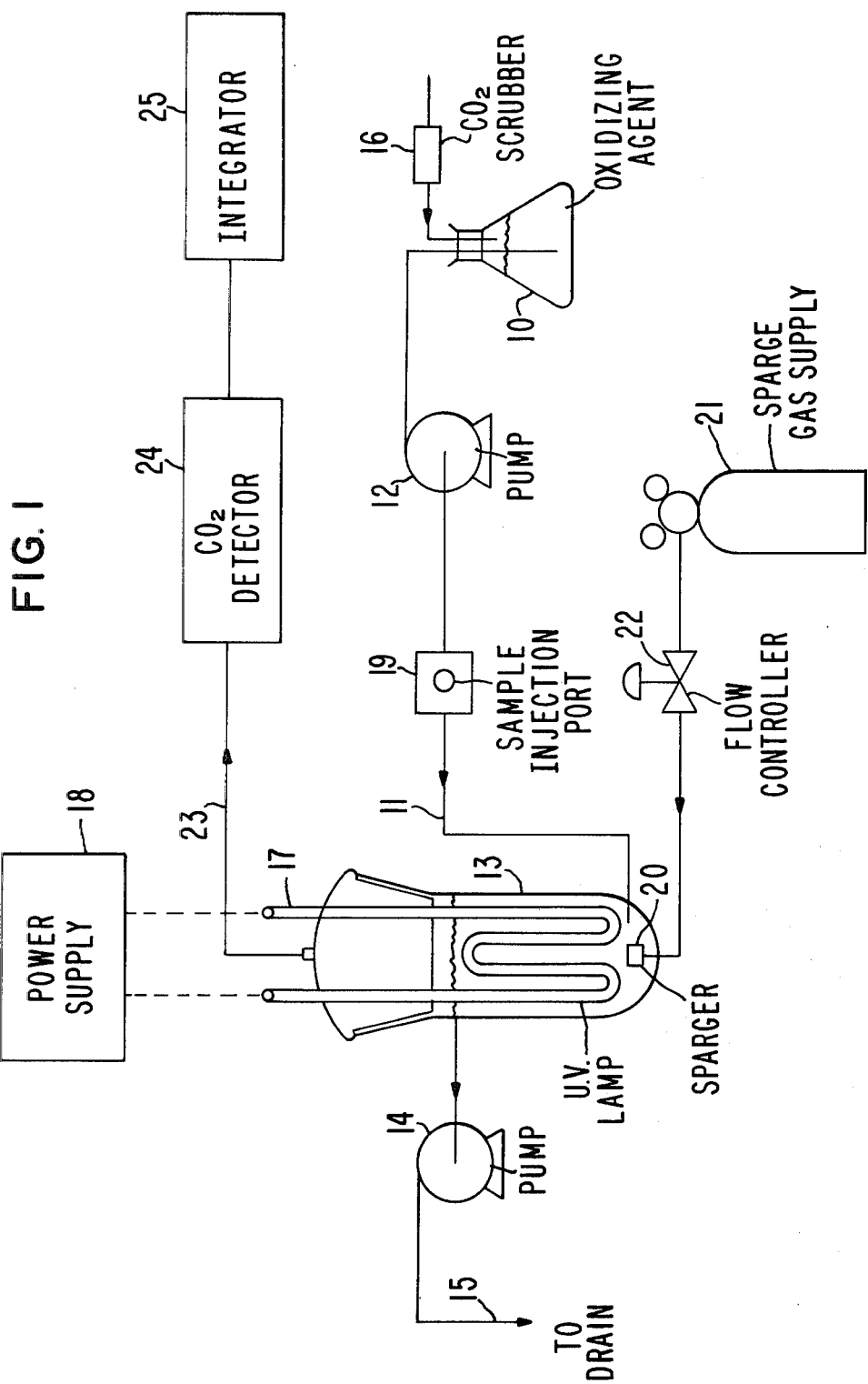
FIG. 1 is a schematic representation of a system for determining total carbon in each one of a plurality of discrete liquid samples.

In the system depicted schematically in FIG. 1, a continuous flow of a precipitate-free aqueous solution containing an oxidizing agent and mercuric monohalide ion is pumped from a reservoir 10 via a flowline 11 by means of a pump 12 into a reactor 13. Although the volume of the reactor 13 is not critical to the practice of this invention, a typical volume for the reactor 13 is 0.1 liter. A pump 14 is provided to withdraw liquid from the reactor 13 via a flowline 15 to a drain at a rate sufficient to maintain a substantially constant liquid level in the reactor 13.

The oxidizing agent in the aqueous solution in the reservoir 10 may comprise persulfate ion $S_2O_8^{--}$, which is formed by dissolving a salt of persulfate in distilled or deionized water. The salt of persulfate most often used is potassium persulfate, but comparable oxidation efficiencies can be obtained using sodium persulfate or ammonium persulfate. An aqueous solution of hydrogen peroxide would also provide a suitable oxidizing agent, viz., hydroxy free radical .OH, for the practice of this invention. A carbon dioxide scrubber 16 is provided to remove carbon dioxide from air entering the reservoir 10, so that the liquid being pumped from the reservoir 10 is substantially carbon-free.

A mercury vapor lamp 17 having a quartz envelope is immersed in the aqueous solution inside the reactor 13. The lamp 17 is powered by an electrical power supply 18 to emit electromagnetic radiation, which promotes oxidation of organic carbon compounds by the oxidizing agent in the reactor 13. Radiation emitted at the 2537-angstrom wavelength and at the 1849-angstrom wavelength is highly effective in promoting oxidation of organic matter by the oxidizing agent. The 2537-angstrom wavelength is in the ultraviolet region of the electromagnetic spectrum, and the 1849-angstrom wavelength is often characterized by chemists as being in the vacuum-ultraviolet region.

The mercury vapor lamp 17 is preferably of folded tubular configuration, and is designed to provide as much surface area as practicable in direct contact with the aqueous solution in the reactor 13. In a preferred embodiment according to this invention, the reactor 13 is a generally cylindrical glass structure that can be filled to a selected level with aqueous solution from the reservoir 10, which provides a constantly replenished supply of oxidizing agent to the reactor 13. The mercury vapor lamp 17 is a quartz tube folded to provide a plurality of elongate sections of substantially uniform cross-sectional area. The elongate sections of the lamp 17 are immersed in the aqueous solution in the reactor 13, and extend parallel to each other and parallel to the cylindrical axis of the reactor 13.

In the embodiment shown in FIG. 1, each one of a plurality of aqueous samples is introduced in succession (as by syringe injection) into the flowline 11 through a sample injection port 19. Each sample is then conveyed into the reactor 13 by the solution flowing from the reservoir 10. Injection of the samples into the flowline 11 rather than directly into the reactor 13 eliminates the need to provide an injection port on the reactor 13, thereby enabling relatively fragile glass to be used in fabricating the reactor 13.

Inside the reactor 13, the ultraviolet radiation and the oxidizing agent cause oxidation of organic matter in each sample. Where the oxidizing agent comprises persulfate ion $S_2O_8^{--}$, the ultraviolet radiation $h\nu$ converts the persulfate ion to sulfate free radical $SO_4^-$. by the reaction $S_2O_8^{--} + h\nu \rightarrow 2SO_4^-$.. The ultraviolet radiation also excites the organic carbon compounds R to an excited state R* by the reaction $R + h\nu \rightarrow R^*$. The sulfate free radical then oxidizes the excited organic carbon compounds by the reaction $R^* + SO_4^-. + H_2O \rightarrow nCO_2 + \ldots$. Because a fresh supply of persulfate ion is continuously being delivered to the reactor 13, sufficient sulfate free radical is always available to cause complete oxidation of the organic matter in each succeeding sample that is injected into the flowline 11. Where the oxidizing agent comprises hydroxy free radical .OH, the .OH results from the dissociation of hydrogen peroxide due to ultraviolet radiation by the reaction $H_2O_2 + h\nu \rightarrow 2.OH$.

The carbon dioxide $CO_2$ produced by the oxidation process occurring in the reactor 13 is sparged from the reactor 13 by a carbon-free sparging gas that is introduced into the aqueous solution near the bottom of the reactor 13 by a sparger 20, which is coupled to an external gas supply 21. The rate of introduction of the sparging gas into the reactor 13 can be controlled by a flow controller 22. It is important that the sparging gas flow rate through the aqueous solution in the reactor 13 be constant if an infrared detection means is used to measure carbon dioxide produced by the oxidation process, as is discussed more fully hereinafter. Typically, an inert gas such as nitrogen is used as the sparging gas. However, a carbon-free gas containing molecular oxygen (e.g., air) could also be used as the sparging gas.

Gaseous products of the oxidation process occurring in the reactor 13 are sparged from the reactor 13 and passed via a flowline 23 to a conventional carbon dioxide detector 24, which for example may be a non-dispersive infrared detector, a coulometric titration cell, or a conductometric measuring apparatus. During the time interval while organic matter in a sample is being oxidized in the reactor 13, the carbon dioxide detector 24 generates a dynamic time-varying signal proportional to the amount of carbon dioxide detected. Over the complete oxidation interval, the signal generated by the carbon dioxide detector 24 exhibits a waveform that starts at a "zero" or baseline value when the sample is first injected, rises to a peak, and then falls back to the "zero" or baseline value when all of the organic matter in the sample is consumed by the oxidation process. Since the flow rate of aqueous solution drawn from the reservoir 10 into the reactor 13 remains constant, the "zero" or baseline value of the signal generated by the carbon dioxide detector 24 uniformly accounts for any background carbon in the aqueous solution.

The signal generated by the carbon dioxide detector 24 can be integrated over the complete oxidation interval for each sample by conventional electronic integrator circuitry 25 to provide a measure of total carbon dioxide generated by oxidation of the sample in the reactor 13. Total carbon dioxide detected for a sample is a measure of total organic carbon present in the sample. Automation of the sample injection technique illustrated in FIG. 1 would require mechanical apparatus and electronic instrumentation of major complexity. Therefore, an alternative technique has been developed for introducing liquid samples into the reactor 13 automatically. In the embodiment shown in FIG. 2, a pump 201 is provided for withdrawing a quantity of carbon-free liquid from the reactor 13 into an external recirculation line 202 through which the carbon-free liquid is circulated back to the reactor 13. The samples are introduced in succession into the recirculation line 202 by means of a multi-position rotary valve 203, which is coupled to a sample loop 204 by conventional "zero dead volume" fittings. A six-position Teflon rotary valve of the type marketed by Rheodyne, Inc. of Berkeley, Calif. under the designation Type 50 is a suitable valve for the practice of this invention.

The rotary valve 203 is internally configured to provide alternative flow paths for liquid passing therethrough, depending on the rotational position of a rotor portion with respect to a stator portion of the valve 203. As indicated schematically in FIG. 2, a pump 205 draws an aqueous sample from a selected one of a plurality of sample containers 206 via a sample feedline 207 to the valve 203. The rotor portion of the valve 203 is first positioned so that carbon-free liquid from the reactor 13 passes through the valve 203 and returns to the reactor 13 via the flowline 202, while the selected aqueous sample passes through the valve 203 into the sample loop 204 and then back to the valve 203 for exit to a drain. In this way, the sample loop 204 can be "loaded" with a precisely measured slug of sample liquid from the selected one of the containers 206.

After the sample loop 204 has been "loaded" with a slug of sample liquid from the selected one of the containers 206, the rotor portion of the valve 203 is rotated so that further sample liquid from the selected one of the sample containers 206 thereafter passes through the valve 203 for exit to the drain, while carbon-free liquid from the reactor 13 is made to flow through the sample loop 204 in circulating back to the reactor 13. In this way, the slug of sample liquid in the sample loop 204 is displaced by an equal volume of carbon-free liquid, and the slug of sample liquid is conveyed into the reactor 13 by the circulating carbon-free liquid.

With samples having a high concentration of organic material, it is necessary to insure that sufficient oxidizing agent is available to enable complete oxidation of all the organic matter in each sample. In the prior art, samples of high carbon concentration were usually diluted to a carbon concentration in the 50 ppb to 100 ppm range before being introduced into the reactor. However, with the sample introduction technique of the present invention, whether by syringe injection as in FIG. 1 or by rotary valve as in FIG. 2, dilution of a sample of high carbon concentration is unnecessary. Since each sample can be introduced into the reactor in as small a volume as desired, and since a fresh supply of oxidizing agent is continuously being supplied to the reactor 13, there is always sufficient oxidizing agent available to oxidize all the organic matter in each sample. Typically, a 0.6 milliliter per minute flow of a 2% concentration aqueous solution of potassium persulfate or ammonium persulfate into a 100 milliliter reactor 13 is used.

When an aqueous sample contains halide ion, as in the case of seawater or a solution containing a mineral acid such as hydrogen chloride HCl, the halide ion absorbs ultraviolet radiation below 2000 angstroms and thereby suppresses the rate at which oxidation of organic matter in the sample can occur. For a typical seawater sample introduced into a reactor holding 100 milliliters of 2% $S_2O_8^{--}$ ion, the time required in the prior art to oxidize organic matter in the sample with ultraviolet radiation from a mercury vapor lamp was on the order of eight minutes or longer.

The analysis of an aqueous sample for total organic carbon typically takes the form of a graphic time-varying signal indicating the amount of $CO_2$ sparged from the reactor. Total organic carbon in the sample is measured by integrating the $CO_2$ detection signal over the time interval required for complete oxidation of the organic matter in the sample. When the time required to oxidize the organic matter in the sample is as long as eight minutes, precision in the measurement suffers due to "tailing" of the signal. The present invention is an improvement over the prior art, however, in enabling an aqueous sample containing halide ion to be oxidized in much shorter time than was possible in the prior art. The present invention therefore makes possible greater precision in TOC analysis of an aqueous sample containing halide ion, in a shorter analysis time, than was possible in the prior art.

In accordance with the present invention, an aqueous sample containing halide ion is analyzed for TOC by being introduced into an aqueous solution in which an oxidizing agent and mercuric monohalide ion are present without forming an insoluble precipitate; and the solution is irradiated with ultraviolet radiation to promote oxidation of organic matter in the sample. The mercuric monohalide ion forms a complex with the halide ion, thereby effectively removing from the solution the halide ion that would otherwise have interfered with the TOC analysis.

It is a feature of the present invention that use of mercuric monohalide ion does not form an insoluble precipitate in the reagent. Use of $Hg^{++}$ ion, on the other hand, would cause formation of an insoluble precipitate, and the complexing agent would in time be consumed as the precipitate is formed. Furthermore, formation of an insoluble precipitate would tend to remove dissolved organic matter from the sample by coprecipitation, thereby introducing an inaccuracy in the measurement of TOC in the sample.

Mercuric monohalide ion is formed by adding a quantity of mercuric halide and a quantity of mercuric nitrate $Hg(NO_3)_2$ to an aqueous solution containing nitric acid, with the molar concentration of the mercuric halide being at least equal to the molar concentration of the $Hg(NO_3)_2$ to insure that no free mercuric ion $Hg^{++}$ remains available for forming an insoluble precipitate. A slight excess of mercuric halide is recommended. The mercuric monohalide ion used according to this invention may be mercuric monochloride ion $HgCl^+$ or mercuric monobromide ion $HgBr^+$. To form $HgCl^+$, a quantity of mercuric chloride $HgCl_2$ is reacted with a quantity of $Hg(NO_3)_2$ according to the reaction $HgCl_2 + Hg(NO_3)_2 \rightarrow 2HgCl^+ + 2NO_3^-$. To form $HgBr^+$, a quantity of mercuric bromide $HgBr_2$ is reacted with a quantity of $Hg(NO_3)_2$ according to the reaction $HgBr_2 + Hg(NO_3)_2 \rightarrow 2HgBr^+ + 2NO_3^-$.

With a solution containing an oxidizing agent and mercuric monohalide ion according to the present invention, TOC analysis time for a typical seawater sample can be shortened to about four or five minutes, as compared to the eight minutes or longer required when the oxidizing reagent does not contain mercuric monohalide ion.

Figure 2:
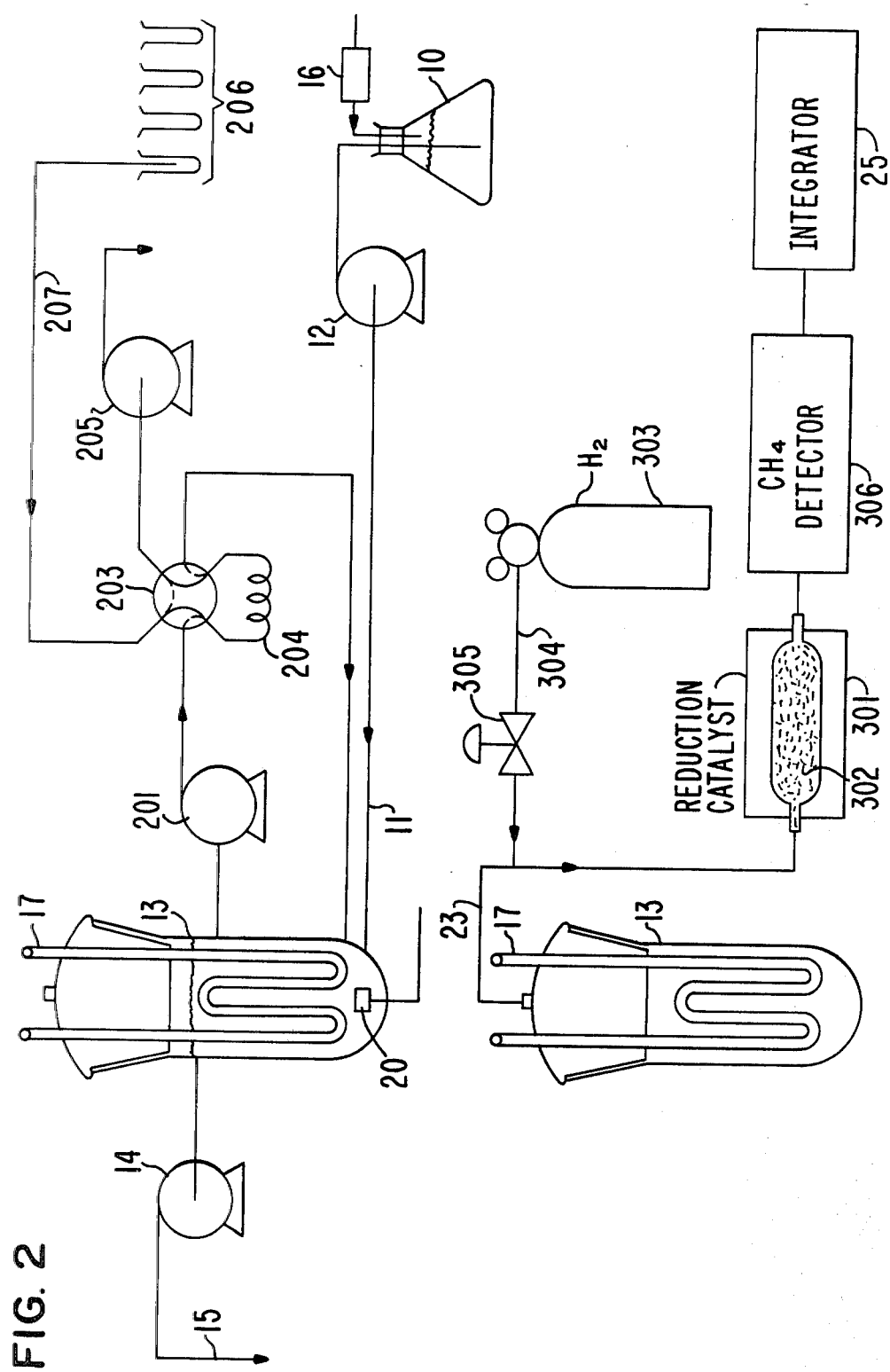
FIG. 2 is a schematic representation of a portion of a system having an alternative means for introducing liquid samples into a reactor.

Unlike the sample injection technique of FIG. 1 where the sample liquid is conveyed into the reactor 13 by a reagent-containing liquid whose flow rate remains constant, the valving technique of FIG. 2 does not utilize a constantly flowing liquid as the means for introducing the sample liquid into the reactor 13. According to the valving technique illustrated in FIG. 2, the flow rate of carbon-free liquid into the reactor 13 falls to zero when the slug of sample liquid sample enters the reactor. If a liquid sample were introduced into the flowline 11 rather than into a separate flowline such as the recirculation line 202, and if the carbon concentration of the liquid sample were less than the carbon concentration of the liquid containing the oxidizing agent (i.e., the liquid in the reservoir 10), then a negative total carbon measurement would be obtained for the sample. The possibility of obtaining negative measurements is obviated, however, by using a carbon-free liquid as the transport means for conveying the liquid sample into the reactor 13. However, where the carbon concentration of the samples to be analyzed is so much higher than the carbon concentration of the liquid in the reservoir 10 that the carbon in the liquid in the reservoir 10 can be ignored, the valve 203 and associated sample loop 204 could be placed in the flowline 11 and the recirculation line 202 would not be needed.

An automated total carbon determination system utilizing the valving technique illustrated in FIG. 2 can be programmed by conventional methods to draw liquid from each one of the sample containers 206 in succession, with the sample loop 204 being "loaded" with a slug of sample liquid drawn from a given one of the containers 206 as soon as the carbon dioxide detector 24 indicates that all organic matter in a slug drawn from the immediately preceding container of sample liquid has been completely oxidized. In this way, each successive slug of sample liquid can be introduced into the reactor 13 as soon as the liquid in the reactor is free of carbon from the preceding sample liquid slug, rather than at some arbitrary time interval following introduction of the preceding sample liquid slug into the reactor 13.

In an alternative embodiment shown in FIG. 3, the gas sparged from the reactor 13 following oxidation of the organic matter in a liquid sample, instead of being passed to a carbon dioxide detector as in FIG. 1, is passed to a reduction chamber 301 containing a catalyst 302 such as nickel or rhodium that converts carbon dioxide to methane in the presence of hydrogen gas. A source 303 of hydrogen gas is coupled to the gas outlet flowline 23 of the reactor 13 by a conduit 304 in which a regulator valve 305 is provided. Carbon dioxide is converted to methane in the reduction chamber 301 by the reaction $CO_2 + 4H_2 \rightarrow CH_4 + 2H_2O$. The methane produced in the reduction chamber 301 is then passed to a methane detector 306, which comprises means for quantitatively measuring total carbon in methane. A suitable methane detector 306 is e.g., a flame ionization detector.

The present invention has been described above in terms of particular techniques for introducing aqueous samples containing halide ion into a reactor, and for measuring total carbon in the gas evolved from oxidation in the reactor of organic matter in each sample. Other particular techniques for implementing the present invention could be devised by workers skilled in the art, and yet be within the scope of the present invention. The above description, therefore, is not to be construed in limitation of the invention but rather is to be understood as illustrative. The scope of the invention is defined by the following claims and their equivalents.

What is claimed is:

1. A process for determining total organic carbon in each one of a plurality of discrete aqueous samples containing halide ion, said process comprising the steps of:
   (a) maintaining a continuous flow via a flowline into a reactor of an aqueous solution that contains an oxidizing agent and mercuric monohalide ion without forming an insoluble precipitate;
   (b) introducing said samples in succession into said reactor;
   (c) irradiating said solution and each sample in said reactor with electromagnetic energy, said electromagnetic energy emanating from a source immersed in said aqueous solution inside said reactor, thereby causing oxidation of organic carbon in each sample;
   (d) causing carbon dioxide produced by oxidation of said organic carbon in each sample to be removed from said reactor; and
   (e) passing the carbon dioxide removed from said reactor to a means for measuring total carbon in said carbon dioxide for each sample.

2. The process of claim 1 wherein said aqueous solution is prepared by mixing said oxidizing agent with a solution containing mercuric monohalide ion, said solution containing mercuric monohalide ion being formed by adding a quantity of mercuric halide and a quantity of mercuric nitrate to an aqueous solution containing nitric acid, the molar concentration of said mercuric halide being at least equal to the molar concentration of said mercuric nitrate.

3. The process of claim 2 wherein said mercuric halide is mercuric chloride, and wherein said mercuric monohalide ion formed is mercuric monochloride ion.

4. The process of claim 2 wherein said mercuric halide is mercuric bromide, and wherein said mercuric monohalide ion formed is mercuric monobromide ion.

5. The process of claim 1 wherein said oxidizing agent contained in said aqueous solution is persulfate ion.

6. The process of claim 5 wherein said persulfate ion is formed by adding a salt of persulfate to water.

7. The process of claim 6 wherein said salt of persulfate is selected from the group consisting of potassium persulfate, sodium persulfate and ammonium persulfate.

8. The process of claim 1 wherein said oxidizing agent is formed by adding hydrogen peroxide to water.

9. The process of claim 1 wherein said irradiating electromagnetic energy has a frequency in a spectral range that includes ultraviolet and vacuum-ultraviolet light.

10. The process of claim 9 wherein said electromagnetic energy emanates from a mercury vapor lamp.

11. The process of claim 1 wherein said carbon dioxide is removed from said reactor by sparging said aqueous solution in said reactor with a carbon-free gas.

12. The process of claim 11 wherein said sparging gas comprises a chemically inert gas.

13. The process of claim 12 wherein said inert gas is nitrogen.

14. The process of claim 11 wherein said sparging gas comprises oxygen.

15. The process of claim 1 wherein total carbon in said carbon dioxide is measured by coulometric titration.

16. The process of claim 1 wherein total carbon in said carbon dioxide is measured by a non-dispersive infrared detector.

17. The process of claim 1 wherein total carbon in said carbon dioxide is measured by conductometric means.

18. The process of claim 1 wherein total carbon in said carbon dioxide is measured by converting said carbon dioxide to methane, and by measuring total carbon in said methane.

19. The process of claim 18 wherein total carbon in said methane is measured by a flame ionization detector.

20. The process of claim 1 wherein said samples are injected in succession into said flowline for conveyance into said reactor by said continuously flowing aqueous solution containing said oxidizing agent and said mercuric monohalide ion.

21. The process of claim 1 wherein a quantity of carbon-free liquid is drawn from said reactor into a recirculation line, and is circulated via said recirculation line back to said reactor; and wherein said samples are introduced in succession into said recirculation line for conveyance into said reactor by said circulating carbon-free liquid.

22. The process of claim 21 wherein a precise quantity of liquid from each sample in succession is allowed by valve means to fill a sample loop, and wherein said valve means further permits a corresponding quantity of carbon-free liquid from said recirculation line to displace each precise quantity of sample liquid in succession from said sample loop into said recirculation line.

23. The process of claim 21 wherein each successive sample is introduced automatically into said recirculation line when said means for measuring total carbon indicates that organic carbon in an immediately preceding sample has been completely oxidized.

* * * * *